US009303283B2

(12) United States Patent
Franciskovich et al.

(10) Patent No.: US 9,303,283 B2
(45) Date of Patent: Apr. 5, 2016

(54) COMBINED STERILIZATION INDICATOR INCUBATOR AND READER SYSTEM

(71) Applicant: American Sterilizer Company, Mentor, OH (US)

(72) Inventors: Phillip P. Franciskovich, Concord, OH (US); Tricia A. Cregger, Fairlawn, OH (US); Paul Vodkin, San Jose, CA (US)

(73) Assignee: American Sterilizer Company, Mentor, OH (US)

( * ) Notice: Subject to any disclaimer, the term of this patent is extended or adjusted under 35 U.S.C. 154(b) by 178 days.

(21) Appl. No.: 14/090,116

(22) Filed: Nov. 26, 2013

(65) Prior Publication Data

US 2015/0147773 A1    May 28, 2015

(51) Int. Cl.
*C12M 1/34* (2006.01)
*C12Q 1/22* (2006.01)
*A61L 2/28* (2006.01)

(52) U.S. Cl.
CPC .... *C12Q 1/22* (2013.01); *A61L 2/28* (2013.01)

(58) Field of Classification Search
CPC ........... C12Q 1/22; A61L 2/28; G01N 31/229
USPC ........................................ 422/28; 435/287.4
See application file for complete search history.

(56) References Cited

U.S. PATENT DOCUMENTS

| | | | |
|---|---|---|---|
| 5,863,790 A | 1/1999 | Bolea | |
| 6,025,189 A | 2/2000 | Bolea et al. | |
| 6,063,591 A | 5/2000 | Bolea | |
| 6,352,837 B1 | 3/2002 | Witcher et al. | |
| 6,768,549 B1 * | 7/2004 | Pfeifer et al. | 356/436 |
| 8,173,388 B2 | 5/2012 | Pasmore et al. | |
| 8,372,624 B2 | 2/2013 | Franciskovich et al. | |
| 2006/0263258 A1 | 11/2006 | Harris et al. | |
| 2010/0081165 A1 | 4/2010 | Pasmore et al. | |
| 2011/0182770 A1 | 7/2011 | Chandrapati et al. | |
| 2012/0149094 A1 | 6/2012 | Smith et al. | |
| 2013/0210069 A1 | 8/2013 | Pederson et al. | |
| 2013/0217040 A1 * | 8/2013 | Brown | G01N 21/6428 435/7.72 |
| 2013/0217107 A1 | 8/2013 | Pederson et al. | |

FOREIGN PATENT DOCUMENTS

BR    PI 0504710-2    1/2007

OTHER PUBLICATIONS

PCT/US2014/054922; PCT International Search Report and Written Opinion of the International Searching Authority dated Nov. 28, 2014.

* cited by examiner

*Primary Examiner* — Kevin Joyner
(74) *Attorney, Agent, or Firm* — Renner, Otto, Boisselle & Sklar, LLP (57) ABSTRACT

A combined sterilization indicator incubator and reader system, including a sterilization indicator vial containing one of a variety of selected biological indicators and a liquid, at least two incubator blocks, each incubator block independently operable to incubate the sterilization indicator vial at a plurality of independently selectable temperatures, each of the incubator blocks including at least one heating element operable to heat the incubator block to any one of the plurality of independently selectable temperatures; a light source, a photodetector and a control system configured to operate the combined system to determine the efficacy of a variety of sterilization processes. The system calculates and compares a slope to a predetermined threshold slope for the biological indicator, and provides output based only on the comparison of the calculated slope to the predetermined threshold slope without first determining either a baseline or a minimum value of the output from the photodetector.

23 Claims, 6 Drawing Sheets

COMBINED STERILIZATION INDICATOR INCUBATOR AND READER SYSTEM

TECHNICAL FIELD

The present invention relates to an apparatus and method for determining the efficacy of a sterilization process. More specifically, the present invention provides a combined sterilization indicator incubator and reader system, in which a sterilization indicator vial may be exposed to sterilization conditions and thereafter may be activated and incubated, and based upon analysis of light emanating from the vial, the efficacy of the sterilization process determined.

BACKGROUND

Various systems for determining the efficacy of sterilization processes are known in the art. There are several types of indicators used in the field, each providing various levels of assurance to the user that the appropriate processing requirements were met.

One of the most important classes of indicators are the biological indicators (BI). BIs provide the highest degree of assurance that sterilization conditions were met within the processor or processed load itself. This type of indicator is designed to represent the worst case for the processing system by providing an extremely high number of highly resistant organisms to that particular process within or on the indicator. Usually spores are the organism of choice for monitoring sterilization systems.

Biological indicators include microorganisms inoculated onto a carrier material. The microorganisms are typically bacterial spores which are known to be very resistant to the particular sterilization medium in which they are to be used. The carrier is placed into a sterilization cycle along with the medical device load. Following completion of the cycle the bacterial spores within the biological indicator are incubated and monitored for growth over periods of up to seven days. Growth of the bacterial spores in the biological indicator indicates that the sterilization process was not efficacious. No growth of the biological indicator confirms that conditions within the sterilizer were adequate to kill at least the number of bacterial spores loaded onto the indicator (e.g., $10^6$ bacterial spores) and therefore provides a level of assurance that the medical device load is sterile.

Due to many factors, there is a need in the hospital setting for determination of the efficacy of the sterilization in the shortest possible timeframe. Prior art systems required 12-48 hours for this determination. More recently, fluorescence has been used to detect the activity of enzymes that are produced by the test organisms by adding a fluorogenic enzymatic substrate to the growth media. This methodology lessens the incubation time from days to hours. However, the main limitation for reducing the incubation time beyond that seen for this methodology is the requirement for the pre-incubation and subsequent fluorescence monitoring of the biological indicator. These indicators have been designed primarily for the purpose of containing the biological indicator cells in a manner and form consistent with the requirements for placement in the sterilizer under evaluation and not necessarily for ease of use in the subsequent fluorescence detection steps.

One such product that permits early evaluation of a biological indicator exists that combines incubation with the simultaneous monitoring of fluorescent emissions, and requires determination of a baseline level of the emissions. This product minimally includes a single heater block that is set to one selected temperature, and a number of vertical holes into each of which one biological indicator may be placed. The heater block has horizontal through-holes which align with transmission panels in a biological sample container in the sample location, so that UV light from UV-emitting lamps may be passed through the biological sample. On a separate, moveable printed circuit board there resides a single detector that must be moved to align with each of the through-holes so that the detector passes in front of each sample location in turn. The movement of the detector is under the control of an on-board processor and requires moving parts. The detector is moved from one such sample site with through-hole to the next in a sequence and readings are taken for each sample present. An algorithm programmed into the controller logic is used to first determine a baseline level of fluorescence and then to detect the presence of fluorescence at a level above the baseline level. Based on the baseline and the reading obtained, an interpretation is made of a PASS (Negative) or FAIL (Positive) nature to advise the user if conditions were met in the sterilizer cycle being evaluated by the biological indicator.

In the prior art cited above, the reliance on moving parts introduces the potential for mechanical failures and/or light path misalignments. The movement of parts can generate or be interfered with by kinetic forces (vibration and mechanical shock) and can create wear on surfaces requiring periodic maintenance and/or recalibration. The presence of a single heat block means that only one temperature can be used by each machine at a given time or may require the purchase of a separate machine for use at different temperatures.

What is needed is a design that eliminates moving parts, wear points and other mechanical aspects that can impact the durability and performance of such a reader incubator, that eliminates variations in alignment of the light source, the biological indicator and the detector, that does not require the determination of a baseline or minimum level of fluorescence prior to initiating reading of test results, while at the same time provides an early and reliable indication of the efficacy of the sterilization process.

SUMMARY

The present invention provides a solution to the foregoing problems of the prior art, while at the same time the invention provides a system that enjoys an early indication of the efficacy of the sterilization process, and retains a high degree of reliability and provides simple but quite flexible use of biological indicators in sterilization processes.

Thus, in one embodiment, the present invention provides a combined sterilization indicator incubator and reader system, including:

a sterilization indicator vial containing a selected biological indicator and a liquid, wherein the sterilization indicator vial comprises a material of construction, a bottom panel, an interior cavity and an outer side surface, both the material of construction and the outer side surface adapted to transmit light emanating from the interior cavity, the bottom panel adapted to transmit light directed onto the bottom panel into the interior cavity;

at least two incubator blocks, each incubator block independently operable to incubate the sterilization indicator vial at a plurality of independently selectable temperatures, each of the incubator blocks comprising:

(a) at least one heating element operable to heat the incubator block to any one of the plurality of independently selectable temperatures;

(b) at least one well, each well associated with one of the heating element, and each well dimensioned to receive and hold the sterilization indicator vial;

(c) a light source positioned with respect to each well to direct source light through the bottom panel into the interior cavity of the sterilization indicator vial when the sterilization indicator vial is in the well;

(d) a photodetector positioned to detect exit light emanating from the interior cavity, the photodetector positioned at an angle relative to a direction from which the source light is directed through the bottom panel of the sterilization indicator vial;

(e) a user interface operably communicating with a control system, the control system including hardware operable to:
 separately control each heating element to operate at a selected one of the selectable temperatures,
 operate the light source,
 operate the photodetector,
 operate the user interface, the user interface operably communicating with the control system to operate the combined sterilization indicator incubator and reader system, and
 calculate and output data to the user interface relating to efficacy of a sterilization process based upon output from the photodetector during the incubation of the sterilization indicator vial.

In one embodiment, the sterilization indicator vial further includes at least one radially outwardly extending support member disposed along at least a portion of the outer side surface.

In one embodiment, each well comprises a number of slots extending radially outwardly from the well, in which the number and position of the slots correspond to the number and position of the at least one support member, and in which each well is adapted to operably receive the sterilization vial in a number of orientations corresponding to the number of slots.

In one embodiment, the sterilization indicator vial is adapted to provide transmission of the exit light emanating from the interior of the sterilization indicator vial without regard to its rotational orientation in the well, provided that the support members are aligned with and received in the slots.

In one embodiment, the angle at which the photodetector is positioned is in the range from about 22° to about 158° relative to the direction from which the source light is directed through the bottom panel of the sterilization indicator vial.

In one embodiment, the light source is an excitation light source of selected output range of wavelength.

In one embodiment, the photodetector is adapted to detect exit light of the selected output range of wavelength emanating from the interior of the sterilization indicator vial.

In one embodiment, the exit light includes both one or more of photoluminescence, phosphorescence or fluorescence and a portion of the source light.

In one embodiment, the plurality of selectable temperatures are in the range from about 20° C. to about 70° C.

In one embodiment, the control system is adapted to operate the user interface to provide user selection of the selectable temperature for incubation of a sterilization indicator vial placed into the well, and to provide indication of any change in the exit light detected by the photodetector when the sterilization indicator vial is placed in the well and incubated.

In one embodiment, each well is adapted to provide contact with at least a substantial portion of the outer side surface of the sterilization indicator vial.

In one embodiment, the photodetector is positioned to detect when the sterilization indicator vial (a) has been activated, (b) is correctly positioned in the well, and/or (c) contains a predetermined fluid level, based on the exit light.

In one embodiment, the system is adapted to provide a signal at the user interface to indicate whether any one or more of (a), (b) or (c) is not met.

In one embodiment, the control system includes hardware configured to, during the incubation, periodically sample output readings from the photodetector and to calculate a slope of a line obtained from a plurality of the sampled output readings, to compare the calculated slope to a predetermined threshold slope for a specific sterilization indicator contained in the sterilization vial, and to provide the output data relating to the efficacy of the sterilization process based on the comparison.

In one embodiment, the control system is configured to provide the output data based only on the comparison of the calculated slope to the predetermined threshold slope without first determining either a baseline or a minimum value of the output from the photodetector.

In one embodiment, the system further includes a separate cover for each incubator block, wherein the cover and the incubator block are configured so that the cover is closeable only when each well is either unoccupied or occupied by a properly placed and activated sterilization indicator vial.

In one embodiment, the present invention relates to a method of determining the efficacy of a sterilization process, including providing the combined sterilization indicator incubator and reader system described above; exposing the sterilization indicator vial to a sterilization process under conditions intended to sterilize the biological indicator; and operating the system to determine whether the sterilization process was efficacious.

In one embodiment, the present invention relates to a method of determining the efficacy of a sterilization process, including:
 providing the combined sterilization indicator incubator and reader system as described above and operating the heating element associated with a selected one of the at least one well at one of the plurality of selectable temperatures;
 exposing the sterilization indicator vial to a sterilization process under conditions intended to sterilize a specific type of biological indicator contained in the sterilization indicator vial;
 activating the exposed sterilization indicator vial and inserting the activated sterilization indicator vial into the selected well;
 confirming that the activated sterilization indicator vial has been activated, is correctly positioned in the selected well, and contains a predetermined fluid level, by directing light through the bottom panel into the interior cavity of the sterilization indicator vial, detecting exit light emerging from the interior cavity with the photodetector, and providing confirmation or lack thereof to the control system;
 after the confirming, incubating the biological indicator in the activated sterilization indicator vial;
 during the incubating, directing source light through the bottom panel into the interior cavity, and operating the photodetector to detect exit light emanating from the interior cavity; and
 operating the control system to calculate and output data to the control system based upon output from the photodetector during the incubating to determine whether the sterilization process was efficacious, and providing a signal at the user interface indicative of the efficacy or lack thereof.

In one embodiment, operating the control system comprises periodically sampling output readings from the photodetector during the incubation, calculating a slope of a line obtained from a plurality of the sampled output readings, comparing the calculated slope to a predetermined threshold slope for the specific type of the biological indicator contained in the sterilization vial, and providing a signal at the user interface based on the comparison.

In one embodiment, the data relating to the efficacy of the sterilization process is based only on the comparison of the calculated slope to the predetermined threshold slope and the calculated slope is determined without first determining either a baseline or a minimum value of the output from the photodetector.

In one embodiment, the sterilization process is deemed to have failed when the calculated slope equals or exceeds the predetermined threshold slope.

In one embodiment, two of the sterilization indicator vials are simultaneously incubated at two different temperatures in separate ones of the incubator blocks.

In one embodiment, the exit light detected by the photodetector comprises one or more of photoluminescence, phosphorescence and fluorescence.

Thus, the present invention provides a solution to the foregoing problems of the prior art, as described in detail in the following. As will be understood, the present disclosure provides an exemplary description of the invention, which is limited only by the scope of the appended claims.

BRIEF DESCRIPTION OF THE DRAWINGS

The present invention may be useful with a variety of biological indicators used in sterilization indicators. The annexed drawings are intended to provide an exemplary, non-limiting depiction of a suitable sterilization apparatus and to demonstrate the disclosed process, for the purpose of providing a better understanding of the invention, and are not intended to be limiting in any way. In the annexed drawings, like parts and features may have like reference numbers.

It should be appreciated that for simplicity and clarity of illustration, elements shown in the Figures have not necessarily been drawn to scale. For example, the dimensions of some of the elements may be exaggerated relative to each other for clarity. Further, where considered appropriate, reference numerals have been repeated among the Figures to indicate corresponding elements.

Furthermore, it should be appreciated that the structures and process steps described herein may not form a complete process flow for producing an end-useable combined sterilization indicator incubator and reader system. The present invention can be practiced in conjunction with apparatus and processing techniques currently used in the art, and only so much of the commonly practiced process steps are included as are necessary for an understanding of the present invention.

DETAILED DESCRIPTION

The present invention provides a solution to the problems of the prior art, and provides a system that enables an early indication of the efficacy, or lack thereof, of the sterilization process. The present invention further provides a high level of reliability and ease of use of the biological indicators in determining the efficacy of the sterilization processes.

As used herein, the term "activate", "activated", and cognate terms, when used with respect to a sterilization indicator vial containing a biological indicator and a liquid containing a growth medium, means that the biological indicator has been combined with the liquid containing the growth medium, so that any microorganisms in the biological indicator that have survived a sterilization process, may be incubated.

As used herein, the term "incubate", "incubated", and cognate terms, when used with respect to a sterilization indicator vial containing a biological indicator and a liquid containing a growth medium, means that the biological indicator has been activated and exposed to appropriate conditions, e.g., temperature, humidity and atmosphere, under which any microorganisms in the biological indicator that have survived a sterilization process can begin to metabolize and grow, so that the indicator function of the sterilization indicator vial can be used to evaluate the efficacy of a sterilization process to which the sterilization indicator vial has been exposed.

Figure 1:
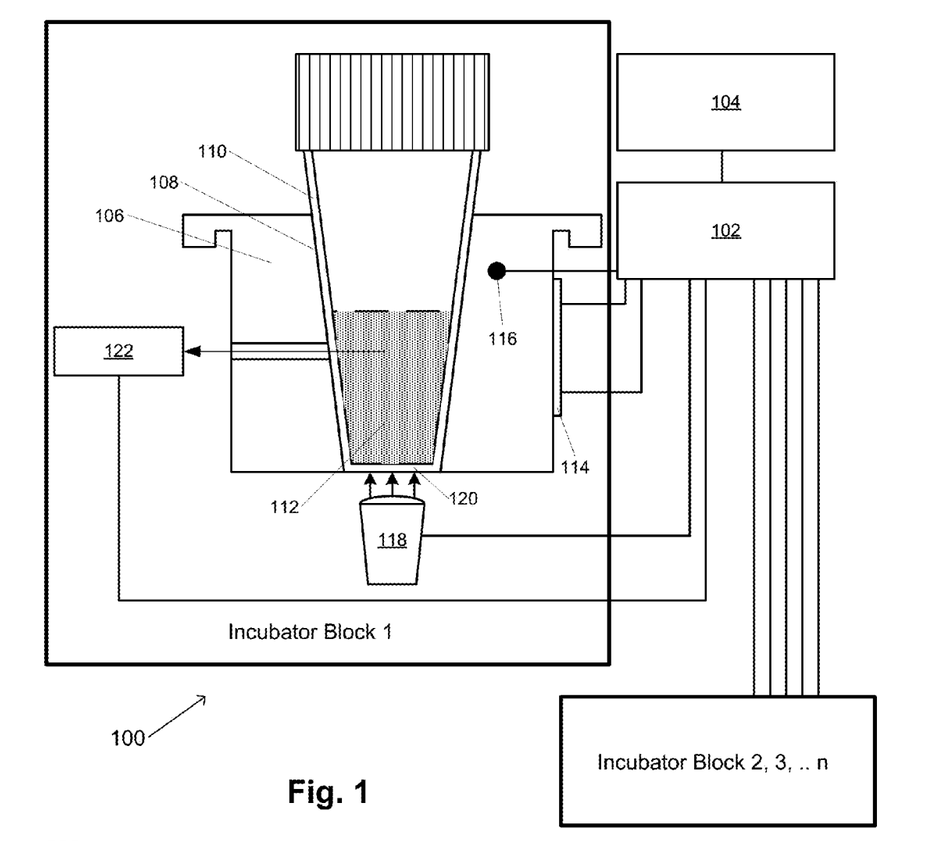
FIG. 1 is a schematic depiction of a combined sterilization indicator incubator and reader system in accordance with an embodiment of the present invention.

FIG. 1 is a simplified schematic representation of a combined sterilization indicator incubator and reader system 100 in accordance with an embodiment of the present invention. As shown in FIG. 1, in accordance with the present invention, the system 100 includes two or more incubator blocks 1, 2, 3, ... n, each incubator block separately and independently controlled by a control system 102, which in turn provides readout and other information to a user interface 104. For simplicity, incubator blocks 2, 3, ... n, are not separately shown, but each such incubator block would be substantially identical to the incubator block 1 shown in FIG. 1.

As depicted in FIG. 1, the incubator block 1 includes a heater chassis 106. The heater chassis 106 includes a well 108 into which an activated sterilization indicator vial 110 fits. In one embodiment, the vial 110 fits into the well 108 so that a substantial portion of the outer sides of the vial 110 are in contact with the walls of the well 108, so as to provide maximum heat transfer to the vial 110 and its contents, i.e., a biological indicator and its appropriate incubation medium 112.

The heater chassis 106 is heated by at least one heating element 114. The heating element 114 is controlled via electrical connections to the control system 102, based on feedback provided to the control system 102 by at least one temperature sensor 116. The temperature sensor 116, in known manner, senses the temperature of the heater chassis 106, provides this temperature information to the control system 102 which in turn determines the timing and intensity of heat applied to the heater chassis 106 by the heating element 114. The control system 102 provides information to the user interface 104 regarding the actual and set points for the temperature of each incubator block, and based on user input via the user interface 104, the control system 102 controls the temperature of the heater chassis 106. The at least one temperature sensor 116 provides temperature information or data to the control system 102.

In accordance with the present invention, each incubator block is adapted to provide heat to incubate one or more vials 110 at a preselected temperature, independent of the other incubator blocks. Thus, for example, the incubator block 1 may be operated at 37° C., while the incubator block 2 may be simultaneously operated at 57° C., or the incubator block 1 may be operated at 57° C., while the incubator block 2 may be simultaneously operated at 37° C. Both blocks may be operated at the same or different temperatures, and additional incubator blocks may be operated at other temperatures. It is noted that the 37° C. and 57° C. temperatures are merely exemplary of practices at the present time, and the possible range of temperatures are not limited to these examples, but can be any temperature at which a given microorganism may be incubated.

Referring still to FIG. 1, each incubator block further includes a light source 118. As depicted schematically in FIG. 1, the light source 118, in one embodiment, is positioned in the incubator block below the sterilization indicator vial 110, so that source light from the light source 118 passes up through the bottom panel 120 of the vial 110. In FIG. 1, the source light is depicted schematically by the arrows from the light source 118 to the bottom panel 120. The source light passes through the bottom panel 120 and into the biological indicator and incubation medium 112.

As depicted in FIG. 1, the incubator block further includes a photodetector 122. The photodetector 122 is selected to be capable of detecting exit light comprising both source light from the light source 118 and light, such as fluorescence or phosphorescence, emitted by metabolic products of any surviving microorganisms in the biological indicator during incubation. The source light emanating from the interior cavity as exit light may be reflected, scattered or refracted source light. Thus, the exit light may comprise both one or more of photoluminescence, phosphorescence or fluorescence and a portion of the source light.

The photodetector 122 may be a general purpose photodetector capable of detecting light across a broad range of wavelengths, or it may be a more "dedicated" photodetector capable of detecting only light of certain selected wavelengths. Suitable filters to narrow the range of wavelengths may be used in either light path. As will be understood, there may be advantages in use of either of these types of photodetectors. While the general purpose photodetector provides a wide range of detectable wavelengths, it may lose some sensitivity due to the need to detect many wavelengths of light. On the other hand, while the dedicated photodetector may be more sensitive at certain selected wavelengths, it is not as versatile as is the general purpose photodetector. The skilled person can select a suitable photodetector as needed.

When the vial 110 is initially inserted into the well 108, the source light from the light source 118 enters the interior space of the vial 110 in which the biological indicator and incubation medium 112 are located. If the liquid level is sufficiently high, either or both native fluorescence or light scattered by the medium 112 may be detected as exit light by the photodetector 122, and the photodetector 122 may provide a signal to the control system 102, by which the control system 102 determines that the liquid level in the vial 110 is adequate. If the sterilization indicator vial is not properly activated, it will not contain a sufficient liquid level, since the incubation liquid will remain in the cap. If the sterilization indicator vial is not correctly positioned in the well, e.g., if it is not all the way down into the well, the source light from the light source will not be scattered, reflected or refracted in the same way it would be if the vial were correctly placed in the well. In one embodiment, the photodetector is positioned to detect when the sterilization indicator vial (a) has been activated, (b) is correctly positioned in the well, and/or (c) contains a predetermined fluid level, based on the exit light. In one embodiment, the system is adapted to provide a signal at the user interface to indicate whether any one or more of (a), (b) or (c) is not met. Thus, for example, the control system 102 may provide an indication to the user interface 104 as to whether or not the liquid level in the vial 110 is sufficient to allow the photodetector 122 to detect exit light produced by any surviving microorganisms contained in the biological indicator. Similar notifications may be made when the vial is not properly activated and/or when the vial is not correctly positioned in the well.

The exit light produced by the surviving microorganisms (if there are any) may include one or more of photoluminescence, phosphorescence and fluorescence. In one embodiment, the photodetector 122 is adapted to detect light from individually selected wavelengths. That is, in this embodiment, the photodetector 122 can be selected to detect the exit light at one of a variety of different wavelengths, or one or more ranges of different wavelengths, thus making it useful for many different types of sterilization indicators. The above-mentioned light filters may also be used to select wavelengths to be detected.

In one embodiment, the photodetector 122 is adapted to detect exit light scattered by the liquid in the vial 110, where the exit light is of substantially the same wavelength as the excitation (source) light from the light source 118, in which the source light has a wavelength in a selected range of wavelengths. The source light may be referred to as excitation light, since it may function to excite molecules in the liquid in the vial, thereby to produce one or more of photoluminescence, phosphorescence or fluorescence. The range of wavelengths of the source light may be selected based on the specific microorganism and the reporter gene or reporter protein or other reporter molecule used in the biological indicator employed in the specific sterilization indicator vial 110 used in a particular sterilization process. In actual practice, the wavelengths of the source light may be somewhat different than the wavelength of the exit light that the photodetector detects. The source light wavelength selection is generally open, and may depend on the reporter selected and may be varied as needed for various embodiments of the present invention. For example, light scatter, reflection, refraction and the like can be used where the excitation and emission wavelengths are the same. Or, in another embodiment, the wavelengths may vary so that the light emitted by the products of the germinating spores is of a different wavelength than the excitation wavelength, so that only the emitted light is detected by the photodetector. In addition, even though the wavelength of the light source is predominantly in a narrow band, other wavelengths are present over a broader spectrum such that the predominant wavelengths are used to excite the reporter which subsequently emits a detectable signal while other neighboring wavelength(s) can be used for other uses e.g. detection, placement and medium volume.

Thus, both the excitation wavelength and the wavelengths that the photodetector 122 can detect may be varied as needed to provide for use of a wide range of biological indicators in the sterilization indicator. The photodetectors described herein are known in the art and can be suitably selected by the skilled person.

As shown in FIG. 1, the photodetector 122 is controlled by and provides data to the control system 102, and this control and data provision may involve and include the user interface 104. Thus, for example, the user interface 104 may include input capability by which an operator of the system can select the appropriate wavelength of the source light provided by the light source 118. As another example, the user interface 104 may include readout of the intensity and/or wavelength of exit light emanating from the interior cavity of the vial 110, and this readout may relate to either or both of the reflected, refracted or scattered source light used for determination of the proper fill level, activation state or positioning of the vial 110 and of the light produced by the microorganisms, which light produced by the microorganisms may be one or more of photoluminescence, phosphorescence and fluorescence. In one embodiment, the user interface may include input for selection of the type of microorganism used in the biological indicator, and the system may be programmed to automatically set the photodetector 122 to detect exit light of the appropriate wavelength, and/or to set the incubation temperature.

Although not described in detail, the foregoing description of the incubator block 1 applies independently to the incubator block 2 and any additional incubator blocks that may be part of the overall system of embodiments of the present invention.

In accordance with embodiments of the present invention, the photodetector 122 may be oriented at a range of selected angles to the direction of the source light from the light source 118. In one embodiment, the photodetector 122 is positioned at an angle in the range from about 22° to about 158° relative to the direction from which the source light is directed through the bottom panel of the sterilization indicator vial 110, in one embodiment, the photodetector 122 is positioned at an angle in the range from about 45° to about 135° relative to the direction from which the source light is directed through the bottom panel of the sterilization indicator vial 110, and in another embodiment, the photodetector 122 is positioned at an angle in the range from about 60° to about 120° relative to the direction from which the source light is directed through the bottom panel of the sterilization indicator vial 110, and in one embodiment, the photodetector 122 is positioned at an angle substantially orthogonal, i.e., about 90°, relative to the direction from which the source light is directed through the bottom panel of the sterilization indicator vial 110.

In accordance with various embodiments of the present invention, the material of construction of the bottom panel and the side panel of the vial 110 is selected to allow source and/or exit light of selected wavelengths to pass through the bottom and side panels of the vial 110. As will be understood by the skilled person, the material of construction of the sterilization indicator vial 110 must be compatible with the sterilant used in the sterilization process, as well as being capable of allowing the light to pass through it. Thus, for example, the material of construction of the sterilization indicator vial may be one or more of glass, quartz, a polymer (e.g., polycarbonate, polypropylene, polyethylene, polystyrene, polyester, polymethyl methacrylate (PMMA or acrylic), acrylonitrile butadiene styrene (ABS), cyclo olefin polymer (COP), cyclo olefin copolymer (COC), polysulfone (PSU), polyethersulfone (PES), polyetherimide (PEI), polybutyleneterephthalate (PBT), polyethyleneterephthalate (PET), etc.).

Figure 2:
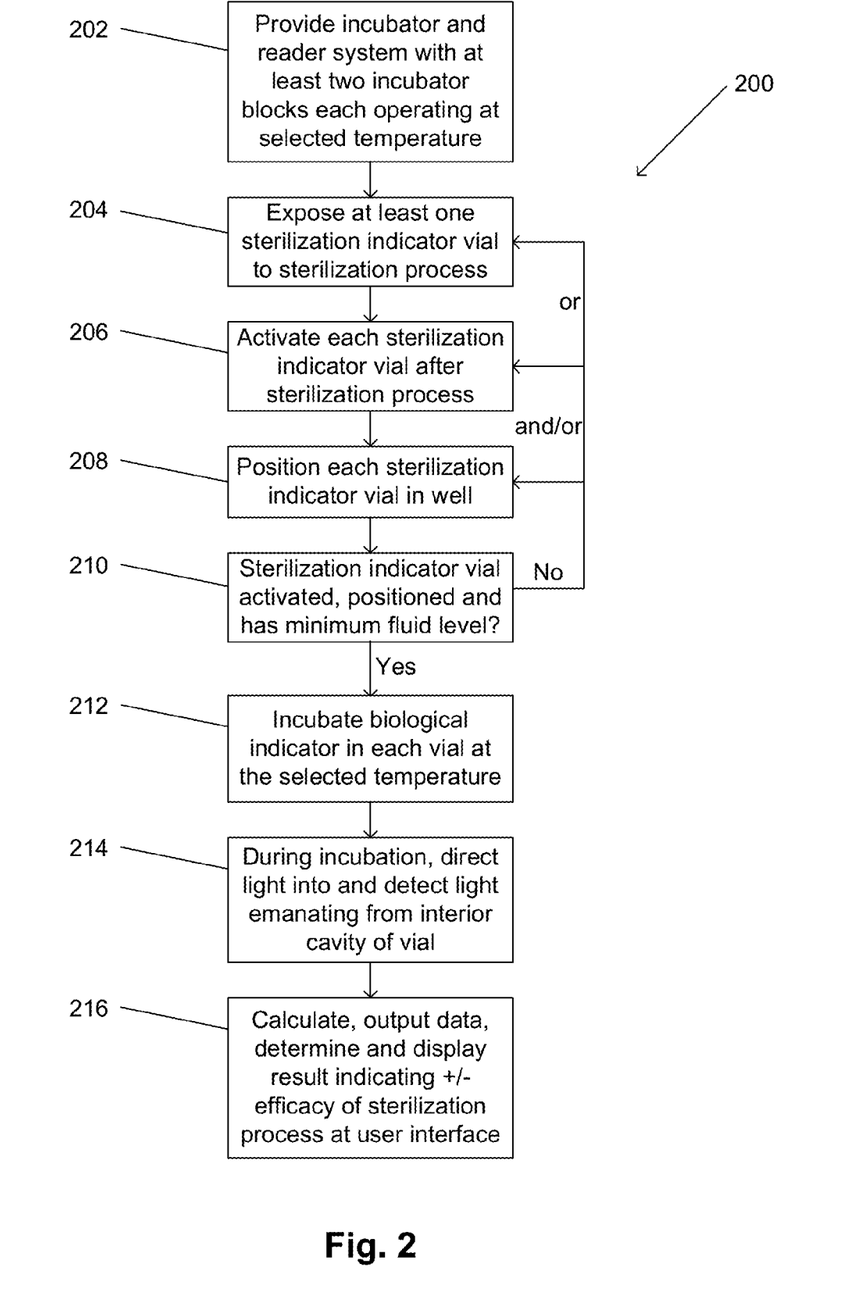
FIG. 2 is a schematic flow chart depicting a process in accordance with an embodiment of the present invention.

FIG. 2 is a schematic flow chart depicting a process 200 in accordance with an embodiment of the present invention. As depicted in FIG. 2, a process in accordance with the present invention may include the following steps. First, in a step 202, there is provided an incubator and reader system with two or more incubator blocks, for example, such as the system 100 described with respect to FIG. 1. Next, in a step 204, at least one sterilization indicator vial, e.g., the vial 110 from the system 100, is exposed to a sterilization process in known fashion. The sterilization process may be suitably selected by persons of skill in the art.

Following exposure of the vial to the sterilization process, as shown in step 206, the exposed sterilization indicator vial(s) is/are activated following the sterilization process. Next, as shown in step 208, each activated vial is positioned in an individual well in one of the incubator blocks of the incubator and reader system.

Following the activation and placement of the vial in steps 206 and 208, in a step 210, the system checks to determine and confirm that the sterilization indicator vial is properly activated, positioned and contains a sufficient amount of incubator liquid to fill the vial to a minimum fluid level. The minimum fluid level is that level which allows the photodetector to detect exit light emanating from the interior cavity of the vial. As will be understood, if the fluid level is too low, the photodetector will not be able to detect the light, and the sterilization indicator will not successfully reflect or report the results of the sterilization process. As shown in FIG. 2, if in the step 210 it is determined that the vial is not properly activated or positioned in the well, steps 206 and/or 208 may be repeated. If the liquid level in the vial is too low, this may be due to improper activation or it could be due to, e.g., leakage and loss of the incubation liquid in the vial, in which case the sterilization indicator vial would be considered to have failed in its purpose of indicating the efficacy or lack thereof of the sterilization process. As shown in FIG. 2, if in the step 210 it is determined that the liquid level in the vial is too low, step 206 and/or step 208 may be repeated, or it may be necessary to repeat the sterilization if the liquid has leaked out of the vial or for some other reason, there is insufficient liquid in the vial, as shown by the arrow in FIG. 2 returning to step 204. This may be avoided, of course, by using a plurality of sterilization indicator vials in any given sterilization process, thereby providing a backup vial for the evaluation process.

Following confirmation that the sterilization indicator vial is properly activated, positioned and filled in step 210, in step 212, with the heating element operating at the selected temperature, the biological indicator in the vial is incubated for a selected length of time at that temperature. The time of incubation may be suitably determined by the skilled person based on the type of biological indicator, but may be predetermined based on the type of biological indicator. In accordance with the present invention, in one embodiment, two of the sterilization indicator vials may be incubated at two different temperatures in separate incubator blocks, at the same time. Additional samples may be placed in empty wells at any time without interfering with any samples already positioned in the incubator blocks.

During the incubation, as shown in step 214, source light from the light source periodically is directed into the bottom of the sterilization indicator vial as described above, and the photodetector detects any exit light produced by or from active, metabolizing microorganisms in the biological indicator and emanating from the interior cavity of the vial. The output from the photodetector is directed to the control system.

As shown in FIG. 2, in step 216, the control system calculates and outputs data to determine whether the exit light emanating from the vial increases during the incubation, which would indicate that there are viable microorganisms, and that the sterilization process did not succeed in killing all of the microorganisms, that is, that the sterilization process was not efficacious. Information indicating the efficacy or lack thereof of the sterilization process is then output to the user interface. The user interface may provide a signal, such as an audible signal or a visible, e.g., warning light, signal to indicate whether the sterilization process was or was not efficacious.

In accordance with embodiments of the present invention, operating the control system comprises periodically sampling output readings from the photodetector during the incubation, calculating a slope of a line obtained from a plurality of the sampled output readings, comparing the calculated slope to a predetermined threshold slope for the specific type of the biological indicator contained in the sterilization vial, and providing the signal at the user interface based on the comparison. In one embodiment, the data relating to the efficacy of the sterilization process are based only on the comparison of the calculated slope to the predetermined threshold slope and the calculated slope is determined without first determining either a baseline or a minimum value of the output from the photodetector. In one embodiment, the sterilization process is deemed to have failed when the calculated slope equals or exceeds the predetermined threshold slope.

Figure 3A:
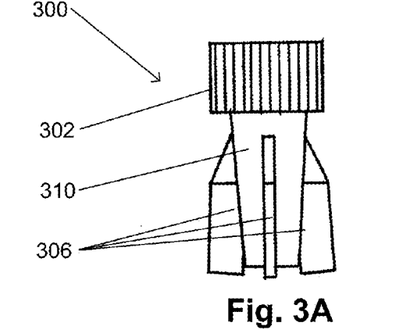
FIGS. 3A and 3B are a side elevational view and a bottom plan view of a sterilization indicator vial suitable for use with embodiments of the present invention.
Figure 3B:
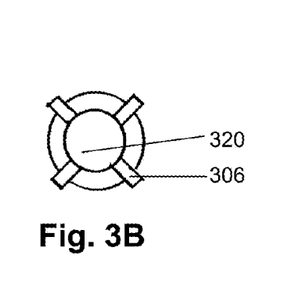

FIGS. 3A and 3B are a side elevational view and a bottom plan view of a sterilization indicator vial 300 suitable for use with embodiments of the present invention. The sterilization indicator vial 300 includes a cap 302, one or a plurality of radially outwardly extending support members 306, and a vial body 310. Although FIGS. 3A and 3B show four support members 306, a sterilization indicator vial in accordance with embodiments of the present invention may have from zero to four such support members 306. As described in more detail below, the support members 306 are designed and intended to fit into slots in the incubator block. In one embodiment, the sterilization indicator vial 300 further includes at least one radially outwardly extending support member 306 disposed along at least a portion of the outer side surface. In one embodiment, each of the at least one well 108 in the incubation block includes at least one slot to align the sterilization indicator vial 300 in a position defined by alignment with the least one support member. In one embodiment, each of the at least one well includes a number of slots extending radially outwardly from the well, and the number and position of the slots in the well correspond to the number and position of the support member(s) 306. In one embodiment, each well is adapted to operably receive the sterilization vial 300 in a number of orientations corresponding to the number of slots, which corresponds to the number of support members. Thus, if there are four equally distributed support members 306, such as shown in FIG. 3B, there are four different, but equivalent, orientations in which the vial 300 can be inserted into the well. In one embodiment, each well is adapted to provide contact with at least a substantial portion of the outer side surface of the sterilization indicator vial.

In one embodiment, the sterilization indicator vial is adapted to provide transmission of exit light emanating from the interior of the sterilization indicator vial without regard to its rotational orientation in the well, provided that the support members are aligned with and received in the slots, if there are support members. It is noted that, while the sterilization indicator vial 300 includes four support members 306, it is possible that the vial 300 has no such support members. In such case, the vial may be rotated in any manner in the well. Thus, in accordance with the present invention, the sterilization indicator vial may be placed in the well in any rotational orientation, and will work equally well in any such orientation.

In one embodiment, the sterilization indicator vial is one described in U.S. Pat. No. 8,173,388 B2, which may be consulted for additional details on this suitable sterilization indicator vial. U.S. Pat. No. 8,173,388 B2 is hereby incorporated herein by reference for its teachings relating to the sterilization indicator vial.

Figures 4A, 4B, 4C:
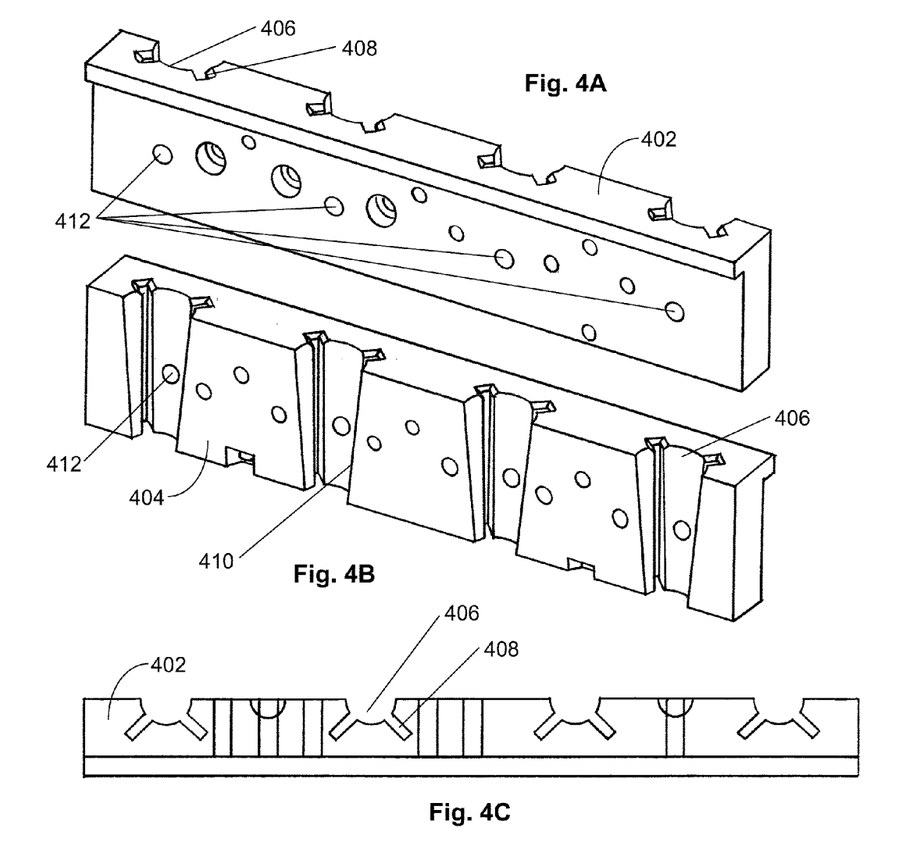
FIGS. 4A, 4B, 4C and 4D are schematic depictions of parts of an incubator block in accordance with an embodiment of the present invention.
Figure 4D:
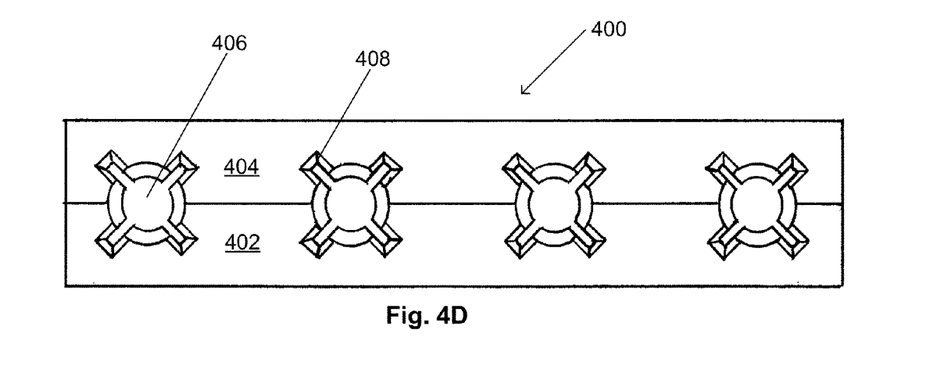

FIGS. 4A, 4B, 4C and 4D are schematic depictions of certain parts of a heater chassis 400 for an incubator block in accordance with an embodiment of the present invention. FIGS. 4A and 4B are perspective views of two halves 402, 404 of a heater chassis for use in an incubator block 400 in accordance with an embodiment of the present invention. FIG. 4C is a bottom plan view of one of the parts 402 or 404. FIG. 4D is a top plan view of the two halves 402, 404, in the position they would occupy in an assembled heater chassis 400.

In the embodiment illustrated in FIGS. 4A and 4B, the parts 402, 404 are actually mirror images of each other; that is, each "half" (e.g., 402) of the heater chassis is identical to the other half (e.g., 404). In this embodiment, the parts 402 and 404 can be made from castings, thus simplifying the manufacture of the heater chassis 400. As will be recognized, the heater chassis could be manufactured from a single block of metal or other material, and the various openings machined into the block, although this would most likely be more expensive.

As shown in FIGS. 4A, 4B, 4C and 4D, each half 402, 404 includes, in this embodiment, four wells 406. Each of the wells 406 in this embodiment includes four slots 408, such as those described above, to align with the support members, e.g., the members 306, on a sterilization indicator vial 300, as described with respect to FIGS. 3A and 3B.

As best shown in FIG. 4B, and similar to the embodiment illustrated in FIG. 1, each well 406 is tapered, top to bottom, and includes inwardly, downwardly tapered sidewalls 410. In one embodiment, the taper of the inwardly, downwardly tapered sidewalls 410 corresponds to the taper of the sidewall of the sterilization indicator vial intended for use with the heater chassis of the incubator block in the system of the present invention.

As shown in FIGS. 4A and 4B, each well 406 includes a passageway 412 for use with the photodetector. In practice, only one of the two passageways 412 needs to be present, but in the illustrated embodiment of FIGS. 4A and 4B, both parts 402 and 404 have such a passageway, as an artifact of the identicality of the two parts 402, 404 in this embodiment. As will be described below with respect to FIG. 5, a photodetector will be aligned with each one of the passageways 412 in one of the two parts 402 or 404, while the passageway on the other of the two parts will be blocked. Other openings in the parts 402, 404 are used, for example, for mounting a heater element, a temperature sensor, or for assembling the heater chassis 400 and other parts of the incubator block.

Figure 5A:
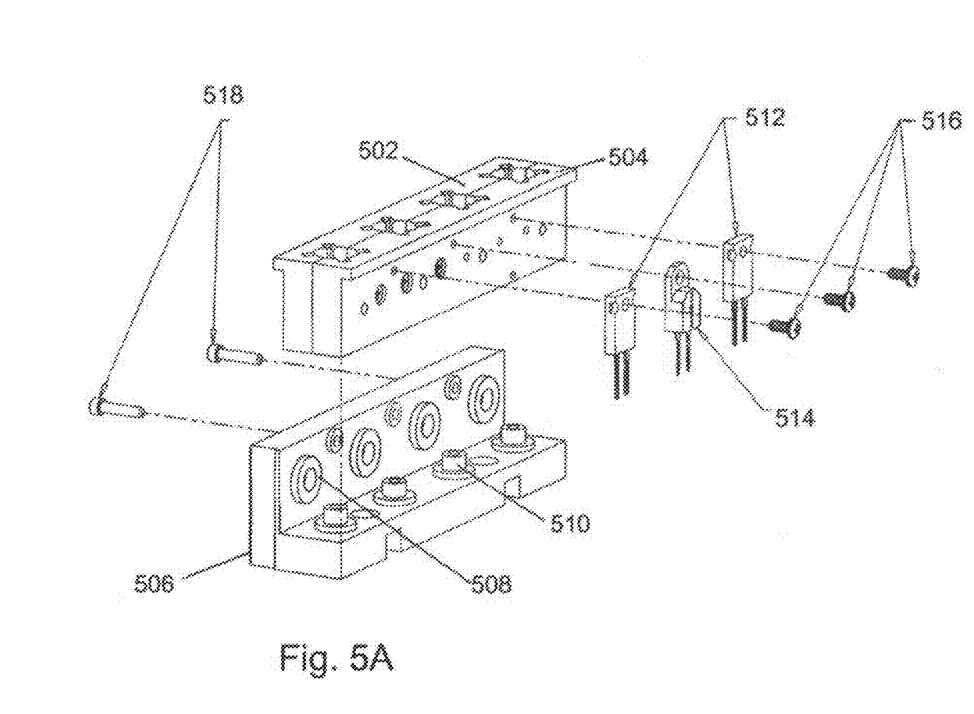
FIGS. 5A, 5B and 5C are schematic depictions of parts of a heater chassis together with operating components of an incubator block for a system in accordance with an embodiment of the present invention.
Figure 5B:
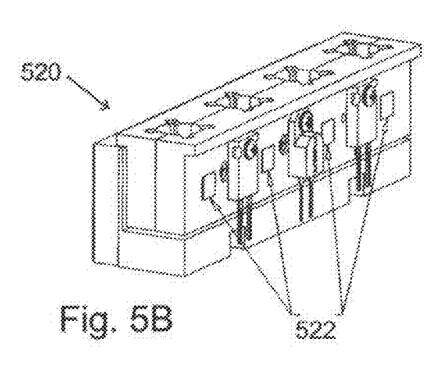
Figure 5C:
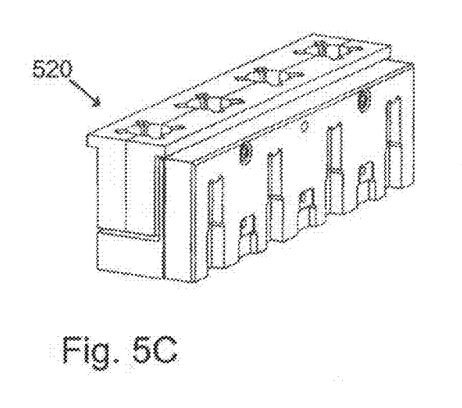

FIGS. 5A, 5B and 5C are schematic depictions of parts of an assembled heater and optical chassis 520, including operating components of an incubator block for a system in accordance with an embodiment of the present invention.

FIG. 5A is a partially exploded perspective view of a heater and optical chassis 520, including parts 502, 504, which correspond to the above-described parts 402 and 404 in FIGS. 4A, 4B, 4C and 4D. FIG. 5A shows an optical chassis 506, which is used together with the heater chassis formed by the parts 502, 504 to form the heater and optical chassis 520. The optical chassis 506 includes a photodetector mount 508 and a light source mount 510. Appropriate photodetector electronics and light source electronics can be mounted in known manner in the mount 508 and the mount 510.

In the embodiment shown in FIG. 5A, the parts for the exploded heater and optical chassis 520 include heater elements 512 and temperature or heat sensor 514. In the embodiment illustrated in FIGS. 5A, 5B and 5C, there are two heater elements 512, but any suitable number of heating elements may be used, as needed to maintain the selected, desired temperature settings for operation of the incubator block. These may be suitably determined by the skilled person. As shown in FIG. 5A, the heater elements 512 and the temperature or heat sensor 514 may be mounted onto the part 504 by screws 516. Similarly, the heater chassis formed of the parts 502, 504 may be both constructed and mounted onto the optical chassis 506 by additional mounting screws 518.

FIGS. 5B and 5C are front (5B) and back (5C) perspective views of an embodiment of the assembled heater and optical chassis 520, in which the heater chassis 502,504 has been attached to the optical chassis 506, and the heaters 512 and heat sensor 514 have been attached to the heater chassis using the screws 516 and 518.

As shown in FIG. 5B, in one embodiment, the unused holes for the photodetector in the part 502 or 504 are covered by a cover 522. In one embodiment, the cover 522 may be any suitable material for blocking light entry into the opening and thus, possibly, to the photodetector, from the side opposite where the photodetector is mounted. Power to the heater elements 512 and readout of temperature data from the temperature or heat sensor 514 is provided by the wires leading from the elements, as shown in FIGS. 5A and 5B, to the control system, e.g., the control system 102 shown in FIG. 1.

Figure 6:
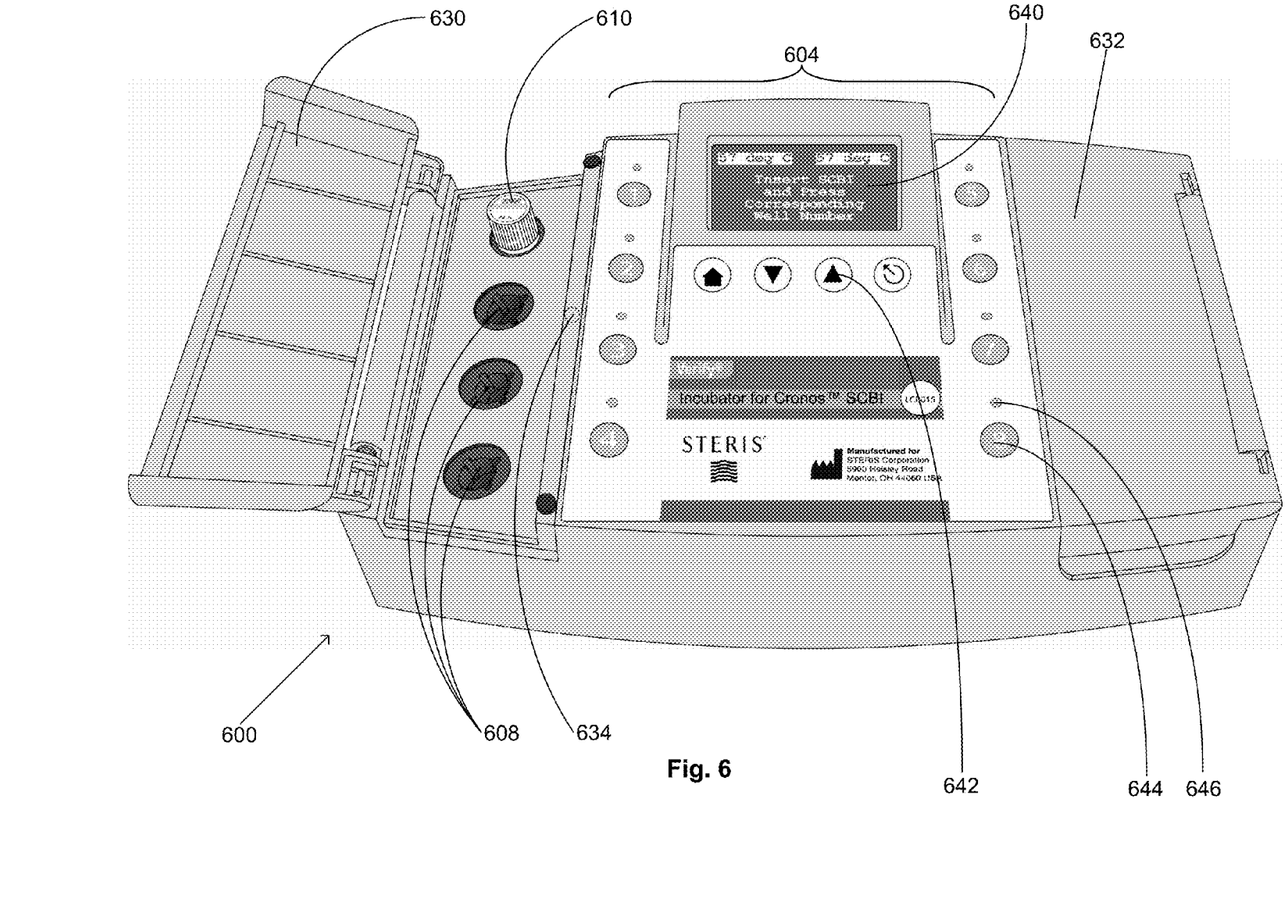
FIG. 6 is a drawing depicting a commercial embodiment of the present invention.

FIG. 6 is a drawing depicting a commercial embodiment of a combined sterilization indicator incubator and reader system 600 in accordance with an embodiment of the present invention. As described with respect to FIG. 1, the system 600 shown in FIG. 6 includes a user interface 604, a plurality of wells 608, each of which is adapted to receive and hold a sterilization indicator vial 610. As described above, system 600 includes a control system that operates the user interface 604 to provide user-selected control of the temperature of incubation of the sterilization indicator vial 610 placed into the well 608. In addition, the control system provides to the user interface 604 an indication of any change in the exit light detected by the photodetector when the sterilization indicator vial 610 is placed in the well and incubated. As described with respect to certain other embodiments, in the embodiment shown in FIG. 6, the wells 608 are adapted to conform to the outer surface of the sterilization indicator vial. Although not well shown in FIG. 6, the wells are shaped to provide contact with at least a substantial portion of the outer surface of the sterilization indicator vial 610. In the embodiment shown in FIG. 6, the system 600 further comprises a cover 630, 632 for each incubator block. In this embodiment, the covers 630, 632 are adapted to be closeable only when each well is either unoccupied or occupied by a properly placed and activated sterilization indicator vial. The system 600 depicted in FIG. 6 includes a magnetic or electrical sensor 634 that is linked to the control system and detects whether the cover 630 is properly closed. In the embodiment shown in FIG. 6, the sensor 634 is depicted in phantom since it is below the surface and not normally visible to the user. In case a vial 610 is not activated or is improperly placed in the well 608, the cover 630 will not close properly and will not make magnetic or electrical contact with the sensor 634. Any such lack of contact with the sensor 634 will be reported to the control system and a suitable indication provided on the user interface 604.

As shown in FIG. 6, the user interface 604 may include a variety of readout and control functionalities, by which operation of the combined sterilization indicator incubator and reader system 600 can be controlled. The user interface may include a readout screen 640, which may show indications of the temperature selected for each incubator block, the status of each individual well with respect to, for example, whether it contains a sterilization indicator vial 610, whether the vial 610 is properly activated, placed and filled with liquid, and whether the photodetector detects any light indicating failure of the sterilization process under review.

Still referring to FIG. 6, the user interface 604 may include selection buttons 642 for use, e.g., in selecting aspects of the incubation, such as time and/or temperature of incubation, identity of the particular biological indicator in the sterilization indicator vial, and status of each well. The user interface may further comprise selection buttons 644 by which the control system and user interface are directed to focus on each individual well 608 one at a time. The user interface may also include an indicator light 646 associated with each well. The indicator light 646 may indicate, for example, presence of a vial 610 in the associated well 608, or that the user interface and the screen 640 are presently indicating conditions for the well 608 for which the indicator light 646 is lit. Although not separately shown in FIG. 6, in one embodiment, the user interface further includes an audible and/or visible alarm set to be activated to warn the user that a positive result has been obtained in one or more wells. Such alarm may include causing the selection button 644 and/or the indicator light 646 to flash on and off, with or without an additional audible alarm sound, such as a buzzer, bell or electronic beeping. The foregoing elements of the user interface 604 are exemplary only, and additions to or deletions from the various components described here may be made by the skilled person as needed for particular applications.

FIGS. 7A, 7B, 7C and 7D depict examples of various indications that may be displayed on the screen 640 of the user interface of FIG. 6, regarding the status of the wells 608 and the vials 610 that may be placed in the wells. As shown in each of FIGS. 7A, 7B, 7C and 7D, the screen 640 shows the set-point temperatures of each of the two incubation heaters in this embodiment. As will be understood, in a system with more than two incubation (left and right) heaters, the set-point temperature of each separate incubation heater would be separately shown on the display 640.

Figure 7A:
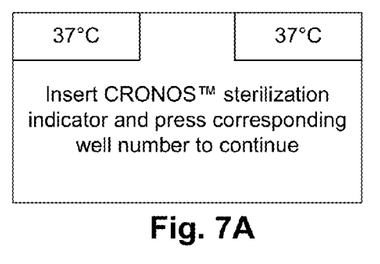
FIGS. 7A, 7B, 7C and 7D include examples of various indications that may be displayed on the screen of the user interface of FIG. 6.

FIG. 7A illustrates an example of a screen in an initial state in which both incubation heaters are set to incubate at 37° C. In this example, the screen 640 instructs the user to insert a sterilization indicator vial (here designated CRONOS™, the trademark for the commercial embodiment of a sterilization indicator vial, from STERIS Corporation, in accordance with an embodiment of the present invention), and then to select the corresponding well number by pressing the appropriate selection button 644, to begin the process of incubating and reading the sterilization indicator vial inserted into the well and then to monitor signal data to be processed in accordance with an embodiment of the present invention.

Figure 7B:
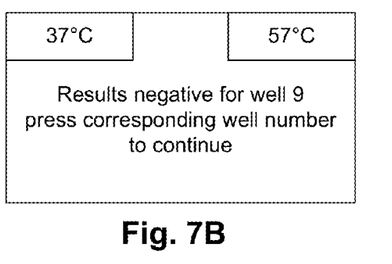

FIG. 7B illustrates an example of a screen in a post-incubation and post-read state, in which one incubation heater is set to incubate at 37° C. and the other incubation heater is set to incubate at 57° C. In this example, the screen 640 informs the user that the results for well 9 were negative, and instructs the user to acknowledge the result by pressing the corresponding selection button 644 to continue.

Figure 7C:
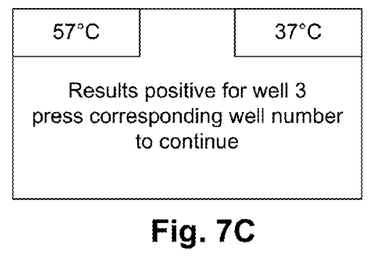

FIG. 7C illustrates an example of a screen in a post-incubation and post-read state, in which one incubation heater is set to incubate at 57° C. and the other incubation heater is set to incubate at 37° C. In this example, the screen 640 informs the user that the results for well 3 were positive, and instructs the user to press the corresponding selection button 644 to silence an alarm that was activated to warn the user that a positive result had been obtained for the sterilization indicator vial in well 3.

Figure 7D:
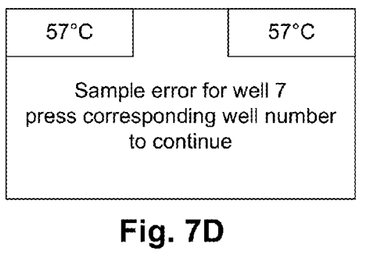

FIG. 7D illustrates an example of a screen in an error state, in which both incubation heaters are set to incubate at 57° C. In this example, the screen 640 informs the user that the sterilization indicator vial in well 7 is in an error state, and instructs the user to press the corresponding selection button 644 to continue. In one embodiment, upon the user pressing the selection button to continue, the display screen changes to inform the user that the vial in the well 7 is improperly activated, improperly placed in the well, does not contain a sufficient liquid level, or is erroneous for some other reason, so that the operator knows what action needs to be taken to correct the error state.

Figure 8:
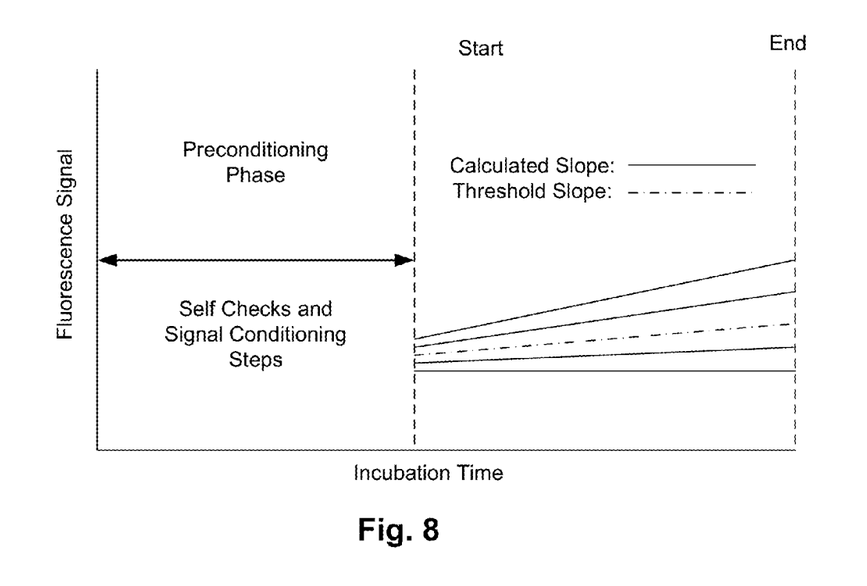
FIG. 8 is a graph showing how the results of the incubation and reading in accordance with an embodiment of the present invention are analyzed to determine whether the sterilization process under evaluation is efficacious.

FIG. 8 includes a graph showing the processes of exemplary incubations and readings in accordance with an embodiment of the present invention, in which sterilization indicator vials have been analyzed to determine whether the sterilization process under evaluation is efficacious. In the embodiment shown in FIG. 8, the light generated by surviving, incubating microorganisms is fluorescence, although the light could be a different type of light, as disclosed above. As shown in FIG. 8, the factory-set threshold slope is represented by the dashed line on the graph, and exemplary slopes for four exemplary incubations are represented by the solid lines on the graph.

As depicted in FIG. 8, the algorithm employed in the system in accordance with the present invention does not require or acquire a baseline reading. The algorithm periodically records data for each well every, e.g., 20 seconds. This ensures that an activated vial contains the appropriate fluid level throughout the incubation. After the appropriate incubation time (e.g., 3900 seconds), the reader begins to put the data into a database. A curve or line is generated from the database to calculate a slope between, e.g., 3900 seconds and 5400 seconds, and this calculated slope is checked against a factory-set threshold slope value. If the calculated slope is above the factory-set threshold slope value, the sterilization indicator vial is deemed positive, indicating that the sterilization process under evaluation was not efficacious, i.e., failed. If the calculated slope is below the factory-set threshold slope value, the incubation continues. Periodically, e.g., every 1-5 minutes thereafter, the slope is again calculated and compared to the threshold slope value. Any calculated slope value above the threshold slope is a positive, indicating that the sterilization event under evaluation has failed. If after two hours of incubation, the calculated slope never exceeds the factory-set slope threshold, the sterilization indicator vial is deemed negative, meaning that the sterilization process under evaluation was successful. It is noted that the factory-set slope threshold value (1) is not determined by an initial read performed for each evaluation of a sterilization cycle, (2) is not specific to a given sterilization indicator vial, (3) is not specific to a specific type of sterilization cycle being evaluated, but (4) is applicable to all sterilization indicator vials that contain the same biological indicator, regardless of the specific type of sterilization cycle being evaluated. In one embodiment, the factory-set slope is slightly positive so that not all slopes with a positive value will be read as positive for growth (and failure of the sterilization process), but only those whose positive calculated slope exceeds the preset and universal minimum positive slope value.

The foregoing factory-set slope provides one of the unique advantages of the present invention, since it provides for more uniform determinations of sterilization efficacy, improves ease of use of the system, and reduces and therefore improves the time required to evaluate any given sterilization process.

While the principles of the invention have been explained in relation to certain particular embodiments, these embodiments are provided for purposes of illustration. It is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the claims.

The invention claimed is:

1. A combined sterilization indicator incubator and reader system, comprising:
   a sterilization indicator vial containing a selected biological indicator and a liquid, wherein the sterilization indicator vial comprises a material of construction, a bottom panel, an interior cavity defining a vertical axis and an outer side surface, both the material of construction and the outer side surface adapted to transmit light emanating from the interior cavity, the bottom panel adapted to transmit light directed onto the bottom panel into the interior cavity the bottom panel being flat and oriented orthogonally to the vertical axis defined by the interior cavity;
   at least two incubator blocks, each incubator block independently operable to incubate the sterilization indicator vial at a plurality of independently selectable temperatures, each of the incubator blocks comprising:
   (a) at least one heating element operable to heat the incubator block to any one of the plurality of independently selectable temperatures;
   (b) at least one well, each well associated with one of the heating element, and each well dimensioned to receive and hold the sterilization indicator vial;
   (c) a light source positioned beneath each well to direct source light vertically up through the bottom panel along the vertical axis defined by the interior cavity of the sterilization indicator vial when the sterilization indicator vial is in the well;
   (d) a photodetector positioned to detect exit light emanating from the interior cavity, the photodetector positioned at an angle relative to a direction from which the source light is directed through the bottom panel of the sterilization indicator vial;
   (e) a user interface operably communicating with a control system, the control system including hardware operable to:
   separately control each heating element to operate at a selected one of the selectable temperatures,
   operate the light source,
   operate the photodetector,
   operate the user interface, the user interface operably communicating with the control system to operate the combined sterilization indicator incubator and reader system, and
   calculate and output data to the user interface relating to efficacy of a sterilization process based upon output from the photodetector during the incubation of the sterilization indicator vial.

2. The system of claim 1, wherein the sterilization indicator vial further comprises at least one radially outwardly extending support member disposed at a position along at least a portion of the outer side surface.

3. The system of claim 2 wherein each well comprises a number of slots extending radially outwardly from the well, wherein the number and position of the slots correspond to the number and position of the at least one support member, and wherein each well is adapted to operably receive the sterilization vial in a number of orientations corresponding to the number of slots.

4. The system of claim 3 wherein the sterilization indicator vial is adapted to provide transmission of the exit light emanating from the interior of the sterilization indicator vial without regard to its rotational orientation in the well, provided that the support members are aligned with and received in the slots.

5. The system of claim 1 wherein the angle at which the photodetector is positioned is in the range from about 22° to about 158° relative to the direction from which the source light is directed through the bottom panel of the sterilization indicator vial.

6. The system of claim 1 wherein the light source is an excitation light source of selected output range of wavelength.

7. The system of claim 1 wherein the photodetector is adapted to detect exit light of the selected output range of wavelength emanating from the interior of the sterilization indicator vial.

8. The system of claim 1 wherein the exit light comprises both one or more of photoluminescence, phosphorescence or fluorescence and a portion of the source light.

9. The system of claim 1 wherein the plurality of selectable temperatures are in the range from about 20° C. to about 70° C.

10. The system of claim 1 wherein the control system is adapted to operate the user interface to provide user selection of the selectable temperature for incubation of a sterilization indicator vial placed into the well, and to provide indication of any change in the exit light detected by the photodetector when the sterilization indicator vial is placed in the well and incubated.

11. The system of claim 1 wherein each well is adapted to provide contact with at least a substantial portion of the outer side surface of the sterilization indicator vial.

12. The system of claim 1 wherein the photodetector is positioned to detect when the sterilization indicator vial (a) has been activated, (b) is correctly positioned in the well, and/or (c) contains a predetermined fluid level, based on the exit light.

13. The system of claim 12 wherein the system is adapted to provide a signal at the user interface to indicate whether any one or more of (a), (b) or (c) is not met.

14. The system of claim 1 wherein the control system includes hardware configured to, during the incubation, periodically sample output readings from the photodetector and to calculate a slope of a line obtained from a plurality of the sampled output readings, to compare the calculated slope to a predetermined threshold slope for a specific sterilization indicator contained in the sterilization vial, and to provide the output data relating to the efficacy of the sterilization process based on the comparison.

15. The system of claim 14 wherein the control system is configured to provide the output data based only on the comparison of the calculated slope to the predetermined threshold slope without first determining either a baseline or a minimum value of the output from the photodetector.

16. The system of claim 1 wherein the system further comprises a separate cover for each incubator block, wherein the cover and the incubator block are configured so that the cover is closeable only when each well is either unoccupied or occupied by a properly placed and activated sterilization indicator vial.

17. A method of determining the efficacy of a sterilization process, comprising:
providing the combined sterilization indicator incubator and reader system of claim 1;
exposing the sterilization indicator vial to a sterilization process under conditions intended to sterilize the biological indicator; and
operating the system to determine whether the sterilization process was efficacious.

18. A method of determining the efficacy of a sterilization process, comprising:
providing the combined sterilization indicator incubator and reader system of claim 1 and operating the heating element associated with a selected one of the at least one well at one of the plurality of selectable temperatures;
exposing the sterilization indicator vial to a sterilization process under conditions intended to sterilize a specific type of biological indicator contained in the sterilization indicator vial;
activating the exposed sterilization indicator vial and inserting the activated sterilization indicator vial into the selected well;
confirming that the activated sterilization indicator vial has been activated, is correctly positioned in the selected well, and contains a predetermined fluid level, by directing light through the bottom panel into the interior cavity of the sterilization indicator vial, detecting exit light emerging from the interior cavity with the photodetector, and providing confirmation or lack thereof to the control system;
after the confirming, incubating the biological indicator in the activated sterilization indicator vial;
during the incubating, directing source light through the bottom panel into the interior cavity, and operating the photodetector to detect exit light emanating from the interior cavity; and
operating the control system to calculate and output data to the control system based upon output from the photodetector during the incubating to determine whether the sterilization process was efficacious, and providing a signal at the user interface indicative of the efficacy or lack thereof.

19. The method of claim 18, wherein the operating the control system comprises periodically sampling output readings from the photodetector during the incubation, calculating a slope of a line obtained from a plurality of the sampled output readings, comparing the calculated slope to a predetermined threshold slope for the specific type of the biological indicator contained in the sterilization vial, and providing the signal at the user interface based on the comparison.

20. The method of claim 19 wherein the data relating to the efficacy of the sterilization process is based only on the comparison of the calculated slope to the predetermined threshold slope and the calculated slope is determined without first determining either a baseline or a minimum value of the output from the photodetector.

21. The method of claim 20 wherein the sterilization process is deemed to have failed when the calculated slope equals or exceeds the predetermined threshold slope.

22. The method of claim 18 wherein two of the sterilization indicator vials are simultaneously incubated at two different temperatures in separate ones of the incubator blocks.

23. The method of claim 18 wherein the exit light detected by the photodetector comprises one or more of photoluminescence, phosphorescence and fluorescence.

* * * * *